United States Patent
Sato et al.

(10) Patent No.: US 6,605,104 B2
(45) Date of Patent: *Aug. 12, 2003

(54) GRASPING FORCEPS FOR ENDOSCOPE (75) Inventors: Yukio Sato, Kodaira (JP); Tsutomu Okada, Kunitachi (JP); Yayoi Ishibashi, deceased, late of Yokohama (JP), by Kenshi Ishibashi, Hitomi Kato Ishibashi, legal representative (73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/831,327

(22) Filed: Mar. 31, 1997

(65) Prior Publication Data
US 2001/0053923 A1 Dec. 20, 2001

Related U.S. Application Data (63) Continuation of application No. 08/505,889, filed on Jul. 24, 1995, now abandoned.

(30) Foreign Application Priority Data

Aug. 2, 1994 (JP) .......................................... H6-181503
Aug. 2, 1994 (JP) .......................................... H6-181504

(51) Int. Cl.[7] .............................................. A61B 17/28
(52) U.S. Cl. ...................... 606/206; 606/207; 294/99.2; 294/100
(58) Field of Search ................................ 606/205, 206, 606/207, 106; 294/100, 99.2

(56) References Cited

U.S. PATENT DOCUMENTS

| | | |
|---|---|---|
| 1,443,086 A | 1/1923 | Muchow |
| 2,114,695 A | 4/1938 | Anderson |
| 4,174,715 A | 11/1979 | Hasson |
| 4,509,517 A | 4/1985 | Zibelin |
| 4,592,347 A | 6/1986 | Mahruki |
| 4,655,219 A | 4/1987 | Petruzzi |
| 5,053,041 A | 10/1991 | Ansari et al. |
| 5,098,440 A | 3/1992 | Hillstead |

FOREIGN PATENT DOCUMENTS

| | | |
|---|---|---|
| DE | 37 09 706 | 10/1987 |
| DE | 39 09 999 A1 | 9/1990 |
| EP | 205228 | 12/1986 |
| WO | WO 85/04320 | 10/1985 |

*Primary Examiner*—Michael H. Thaler
(74) *Attorney, Agent, or Firm*—Armstrong, Westerman & Hattori, LLP

(57) ABSTRACT

A grasping forceps for an endoscope according to the present invention comprises a flexible insertion section, an operating wire passing through said insertion section and adapted to be advanced and retreated in accordance with an operation of an operating section connected to a hand side end of the operating wire, and an elastic grasping section arranged in the leading end portion of said operating wire and composed of at least four elastic grasping members different in length having a habit of so flexing that leading end grasping portions formed at the leading ends of said elastic grasping members spread outwards from a center axis of said insertion section, wherein the leading end grasping portions formed at the leading ends of the plurality of elastic grasping members different in length are spread in a spiral arrangement at the time of spreading of the elastic grasping section. On one hand, at least the leading end grasping portion to be disposed nearest to the insertion section leading end surface and the elastic grasping member having the leading end grasping portion to be disposed remotest from the insertion section leading end surface come in an inclined relationship at the time of accommodating of the elastic grasping section.

20 Claims, 7 Drawing Sheets

GRASPING FORCEPS FOR ENDOSCOPE

This application is a continuation of application Ser. No. 08/505,889 filed Jul. 24, 1995, now abandoned.

BACKGROUND OF THE INVENTION

1. Field of the Invention

The present invention relates to a grasping forceps for an endoscope which is inserted into a channel formed in an endoscope for allowing a treating instrument to pass therethrough and used for grasping and picking out an object such as a foreign body, polypus and so on within a body cavity.

2. Disclosure of the Related Art

Recently, in addition to the medical examination of a body cavity by an endoscope, there has been known such an art that a grasping forceps for an endoscope such as an in vivo inspection forceps, a grasping forceps inserted into a treating instrument passing channel formed in the endoscope is inserted into the body cavity for grasping and recovering a foreign body within a living body or for grasping and picking out cellular tissue to be inspected.

The grasping forceps for the endoscope comprises a flexible insertion section composed of a coil sheath and the like externally covered with, for example a flexible resin tube, an operating wire passing through this insertion section, an operating section connected with the operating wire at its hand-side end, and a plurality of elastic grasping members arranged at the leading end of the operating wire and having a habit of flexing so as to spread outwards.

Figure 1A:
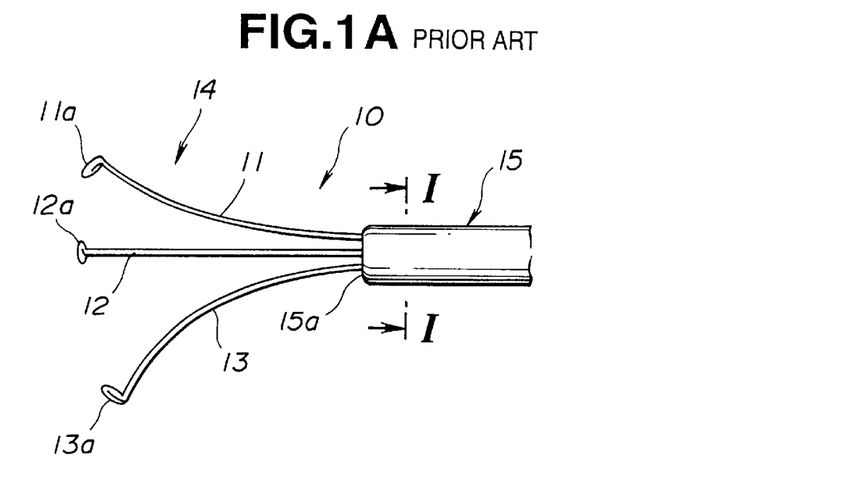
FIG. 1A is a view showing an elastic grasping section in the spread state of the grasping forceps for the endoscope having the elastic grasping section composed of three elastic grasping members of different lengths.

For example, as shown in FIG. 1(A), a conventional grasping forceps 10 for an endoscope has an elastic grasping section 14 composed of three elastic grasping members 11, 12, 13. These elastic grasping members 11, 12, 13 are connected to the leading end of the operating wire. When an operator moves the operating wire toward the leading end side by the manipulation of a finger-engaging member disposed at the hand-side end of the operating wire, the leading end portions of the elastic grasping members 11, 12, 13 are projected from a leading end surface 15a of an insertion section 15. Thereupon, the elastic grasping section 14 spreads outwards from the center axis of the insertion section 15 owing to the elastic restoring forces of the respective elastic grasping members 11, 12, 13.

Further, circular pawl portions 11a, 12a, 13a are formed at the leading end portions of the three elastic grasping members 11, 12, 13 so as to face inwards with respect to the advancing and retreating direction of the operating wire. In the Japanese Utility Model Laid Opened Publication No. 5-62214 disclosed is such a grasping forceps for an endoscope that leading end grasping portions bent nearly perpendicularly relative to a center axis of an insertion section of the grasping forceps for the endoscope are formed at leading ends of a plurality of elastic grasping members constructing an elastic grasping section.

In the grasping forceps 10 for the endoscope, when the finger engaging member is operationally pushed and pulled by the operator, the operating wire is advanced and retreated, so that the leading end portions of the elastic grasping members 11, 12, 13 are projected from and concealed in the leading end surface 15a of the insertion section 15. Thereby, the circular pawl portions 11a, 12a, 13a formed at the leading ends of the elastic grasping members 11, 12, 13 having the habit of flexing are opened and closed.

That is, when the operating wire is operationally pushed, the elastic grasping members 11, 12, 13 are projected from the leading end surface 15a of the insertion section 15, so that the circular pawl portions 11a, 12a, 13a formed at the leading ends of the respective elastic grasping members 11, 12, 13 spread outwards from the center axis of the insertion section 15 owing to the elastic restoring forces of the elastic grasping members 11, 12, 13.

On one hand, when the operating wire is operationally pulled, the elastic grasping members 11, 12, 13 are gradually pulled into the insertion section, so that the spread circular pawl portions 11a, 12a, 13a of the elastic grasping members 11, 12, 13 close gradually to grasp the foreign body and the like.

Lengths of the respective elastic grasping members 11, 12, 13 are adjusted so that the circular pawl portions 11a, 12a, 13a of the elastic grasping members 11, 12, 13 constructing the elastic grasping section 14 are not brought into contact with one another. That is, the circular pawl portions 11a, 12a, 13a are arranged at different positions in the longitudinal direction of the insertion section so as to be converged side by side in line.

Figure 1B:
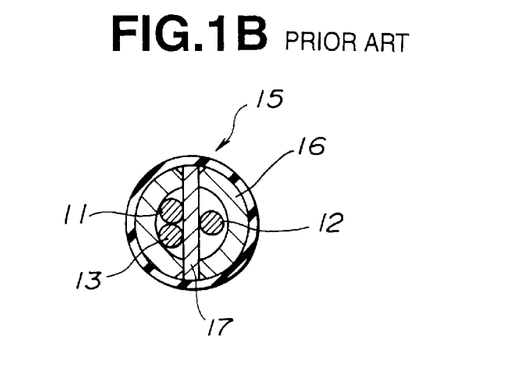
FIG. 1B is a sectional view taken along the I—I line in FIG. 1A.

Incidentally, in FIG. 1B, the symbol 16 designates a leading end member constructing a leading end portion of the insertion section 15 and the symbol 17 does a grasping section dropout preventing pin for preventing the dropping-out of a coupling tube which is fixedly attached to the plurality of elastic grasping members, from the insertion section.

But, since the grasping forceps 10 for the endoscope illustrated in FIG. 1A has the elastic grasping section 14 composed of the three elastic grasping members 11, 12, 13, gaps between the adjacent elastic grasping members become wide. Therefore, it is apprehended that the operator happens to drop the once grasped living body tissue or foreign body through the gaps between the adjacent elastic grasping members within the body cavity.

Further, since flexing degrees of the respective elastic grasping members constructing the elastic grasping section 14 are set to large values, when the wire diameter of the elastic grasping member is made thin, the gaps between the adjacent elastic grasping members become wider. Therefore, practically it is impossible to decrease the wire diameter of the elastic grasping member, so that the flexing degree of the elastic grasping member becomes small. As a result, it is apprehended that the elastic grasping members tend to keep the straight postures to injure the living body tissue at the time of picking out the cellular tissue to be inspected.

Figure 2:
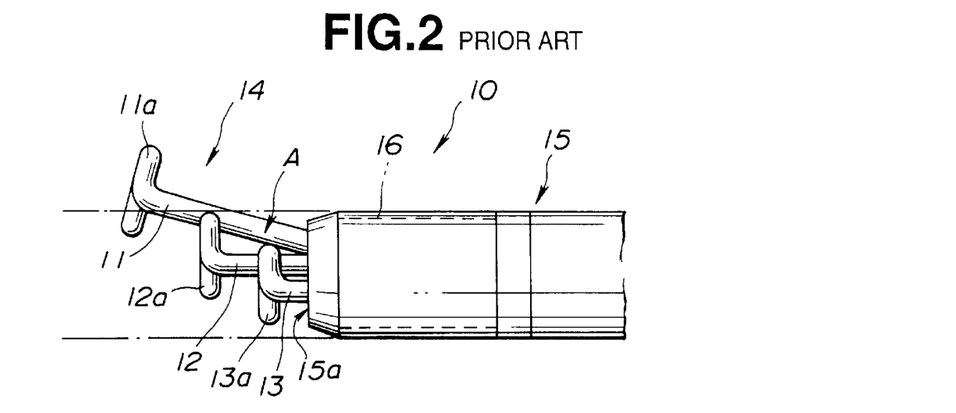

While the elastic grasping members 11, 12, 13 constructing the elastic grasping section 14 are pulled into an internal bore of the cylindrical leading end member 16 of the insertion section 15 by pulling the operating wire of the grasping forceps 10 for the endoscope to the hand side as shown in FIG. 2, when the leading end grasping portion 13a disposed nearest to the insertion section leading end surface 15a is brought into contact with the elastic grasping member 11 having the leading end grasping portion 11a disposed remotest from the insertion section leading end surface 15a as indicated by A in FIG. 2, the elastic grasping member 11 is pushed outwards beyond the extension line (depicted by the alternate long and short dash line) of the outer peripheral surface of the insertion section 15.

When the grasping forceps for the endoscope is removed by the pulling from the endoscope under the condition that the elastic grasping member is pushed outwards beyond the extension line of the outer peripheral surface of the as shown in FIG. 2, it is apprehended that there appear the problems that the inner surface of the treating instrument passing channel of the endoscope is scratched, the elastic grasping portion is deformed, the operability of the grasping forceps becomes worse due to increase in push-pull forces by frictional resistance produced between the leading end grasping portion and the treating instrument passing channel or the grasping forceps for the endoscope is broken by forcibly pulling the grasping forceps for the endoscope from the treating instrument passing channel disregarding the increase in push-pull forces.

OBJECTS AND SUMMARY OF THE INVENTION

It is an object of the present invention to provide a grasping forceps for an endoscope which is provided with an elastic grasping section which is capable of reliably grasp living body tissue or a foreign body without injuring the living body tissue.

It is another object of the present invention to provide a grasping forceps for an endoscope in which elastic grasping members and/or leading end grasping portions seldom entangle with one another at the time of closing a spread elastic grasping section.

It is still another object of the present invention to provide a grasping forceps for an endoscope which doesn't drop a once grasped small living body tissue or foreign body through gaps between adjacent elastic grasping members.

It is a further object of the present invention to provide a grasping forceps for an endoscope in which a leading end grasping section and/or leading end portions of elastic grasping members don't project outwards beyond an outer peripheral surface of an insertion section.

In brief, a grasping forceps for an endoscope according to the present invention includes a flexible insertion section, an operating wire passing through the insertion section, connected at its hand side end to an operating section and adapted to be advanced and retreated in accordance with an operating of the operating section, and an elastic grasping section disposed at the leading end portion of the operating wire and composed of at least four elastic grasping members having different lengths and having a habit of flexing such that leading end grasping portions formed at their leading ends tend to spread outwards from the center axis of the insertion section, wherein at the time of spreading the elastic grasping section, the leading end grasping portions formed at the leading ends of the plurality of elastic grasping members of different lengths spread in a spiral arrangement. On one hand, when the elastic grasping section is accommodated, at least the leading end grasping portion to be disposed nearest to the insertion section leading end surface and the elastic grasping member having the leading end grasping portion to be disposed remotest from the insertion section leading end surface both which constitute the elastic grasping section are in an inclined positional relation.

The other features and advantages of the present invention will become apparent sufficiently to those skilled in the art as disclose is made in the following description thereof.

BRIEF DESCRIPTION OF THE DRAWINGS

FIGS. 1 and 2 show a conventional grasping forceps for an endoscope;

FIG. 2 is a view showing a midway state of the closing of the elastic grasping section of the grasping forceps for the endoscope;

FIGS. 3 through 5 show a first embodiment of the present invention;

FIG. 3 is an explanatory view showing a use condition of a grasping forceps for an endoscope;

FIG. 5 is an explanatory view of the elastic grasping section in the spread state of the grasping forceps for the endoscope;

FIG. 10 shows a third embodiment of the present invention.

FIG. 12 shows a fifth embodiment of the present invention.

DETAILED DESCRIPTION OF THE PREFERRED EMBODIMENTS

A first embodiment of the present invention will be explained with reference to FIGS. 3 through 5.

Figure 3:
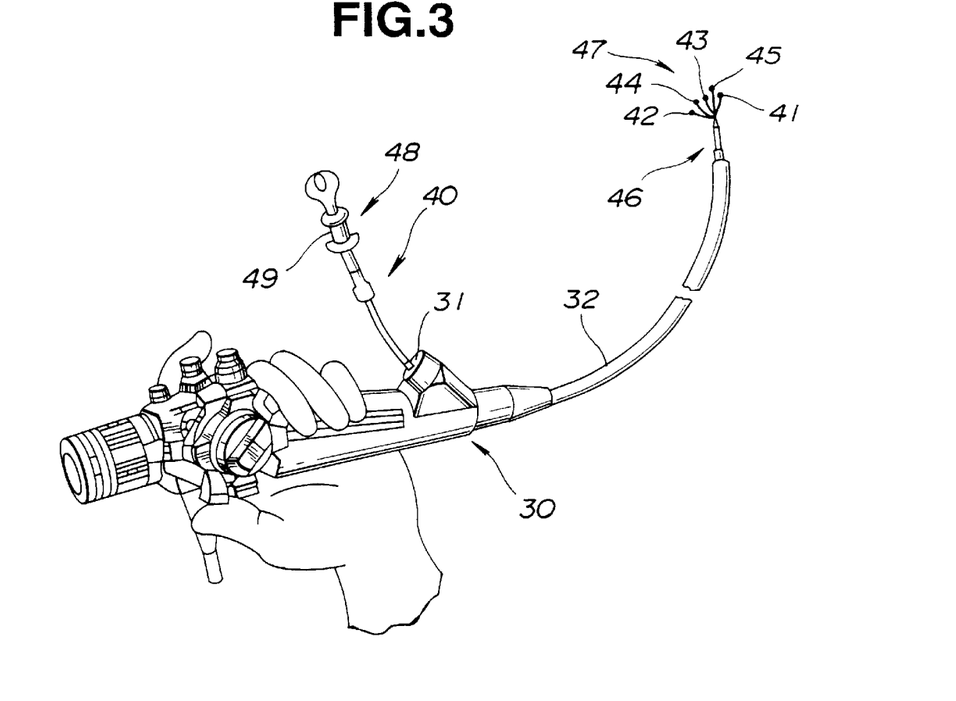

As shown in FIG. 3, a grasping forceps 40 for an endoscope is inserted from a treating instrument insertion opening 31 formed in the endoscope 30 into a forceps passing channel formed within an endoscope insertion section 32 so as to pass through an insertion section 46 for introduction into a body cavity. In this grasping forceps 40 for the endoscope, an elastic grasping section 47 composed of at least four elastic grasping members, for example five elastic grasping members 41, 42, 43, 44, 45 in this embodiment is disposed at the leading end portion of an operating wire passing through an internal bore of the insertion section 46 so as to be able to grasp and pick out an object such as a foreign body, polypus, living body tissue and so on within a body cavity.

The elastic grasping section 47 is adapted to be opened and closed in accordance with pushing and pulling operations of a finger engagement portion 49 of an operating section 48 with which the operating wire is connected at its hand-side end.

Figures 4A, 4B:
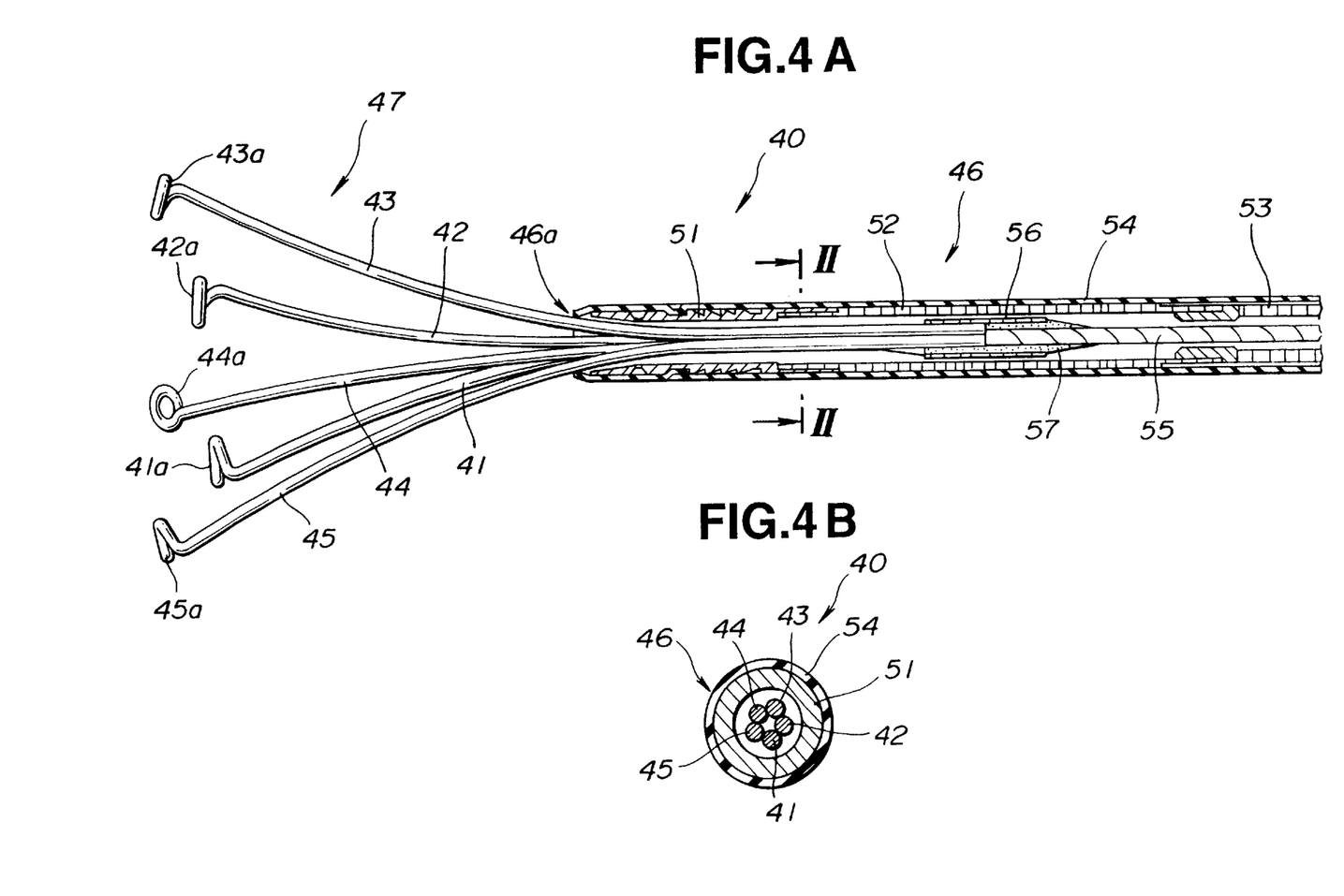
FIG. 4A is a sectional view for explaining a construction of a leading end portion of an insertion section of the grasping forceps for the endoscope.
FIG. 4B is a sectional view taken along the II—II line in FIG. 4A.

That is, as shown in FIG. 4A, the insertion section 46 of the grasping forceps 40 for the endoscope comprises a metallic tubular leading end member 51, a flexible coil sheath 52 on the leading end side and a coil sheath 53 on the base end side which are connected in order with one another, and these leading end member 51, the coil sheath 52 on the leading end side and the coil sheath 53 on the base end side are externally covered with a flexible integument tube 54.

An operating wire 55 is passed through the interior of the insertion section 46, a coupling tube 56 is fixedly connected at its one end to the leading end portion of the operating wire 55 by an adhesive or brazing 57, and five elastic grasping members 41, 42, 43, 44, 45 constructing the elastic grasping section 47 are fixedly connected to the other end portion of the coupling tube 56 by the adhesive or brazing 57. That is, the operating wire 55 and the elastic grasping members 41, 42, 43, 44, 45 are connected integrally through the coupling tube 56.

On one hand, the hand-side end portion of the operating wire 55 is passed through the interiors of the coil sheath 52 on the leading end side and the coil sheath 53 on the base end side so as to be connected to a finger engaging member 49 of the operating section 48 arranged on the hand-side of an operator. Thereby, the operating wire 55 is advanced and retreated by the pushing and pulling operations of the finger engaging member 49, so that the five elastic grasping members 41, 42, 43, 44, 45 can be projected from and concealed into the leading end surface 46a of the insertion section 46.

An elastic stainless steel wire or a spring stainless steel wire is used for the elastic grasping members 41, 42, 43, 44, 45 and has its wire diameter made thin to have flexibility in order to flex largely as well as the habit of flexing so as to spread at least 20 mm outwards from the center axis of the insertion section 46. This is a reason why the limitation diameter within which the living body tissue or the like can be cut by the endoscope is about 20 mm.

Leading end grasping portions for recovering the living body tissue or the like as an object to be grasped within the body cavity are arranged at the leading end portions of the elastic grasping members 41, 42, 43, 44, 45 constructing the elastic grasping section 47. These leading end grasping portions are circular pawl portions 41a, 42a, 43a, 44a, 45a formed by a generally circular curving and are bent inwards with respect to the advancing and retreating direction of the operating wire 55.

The bent portions or the curved portions applied to the leading end surfaces of the circular pawl portions 41a, 42a, 43a, 44a, 45a are finished smoothly for safety's sake so as not to injure the body cavity and so on, and the leading end surfaces to which the bending is applied are opposed to the bent portions so as to prevent hitching.

Lengths of the five elastic grasping members 41, 42, 43, 44, 45 are changed so that the circular pawl portions 42a, 43a, 44a, 45a formed at the leading end portions of the elastic grasping members 41, 42, 43, 44, 45 can be converged side by side in line in the longitudinal direction of the insertion section 46 when the elastic grasping members 41, 42, 43, 44, 45 constructing the elastic grasping section 47 are accommodated within the leading end member 51 and the coil sheath 52 on the leading end side by the pulling operation of the operating wire 55. As shown in FIG. 4B, the five elastic grasping members 41, 42, 43, 44, 45 are arranged so as not to pile within the internal bore of the leading end member 51.

Further, when the elastic grasping section 47 is spread, the elastic grasping members 41, 42, 43, 44, 45 different in length flex according to their habits so that the circular portions 41a, 42a, 43a, 44a, 45a are arranged in the spiral manner.

Functions of the grasping forceps 40 for the endoscope having the above-mentioned construction will be explained First of all, the insertion section 46 of the grasping forceps 40 for the endoscope is made to project from the endoscope leading end portion through the treating instrument passing channel of the endoscope 30 introduced near to the cellular tissue to be inspected under the condition that the operating wire 55 of the grasping forceps 40 for the endoscope has been pulled to the hand side, namely the circular pawl portions 41a, 42a, 43a, 44a, 45a of the elastic grasping section 47 have been closed.

Then, the operating wire 55 is moved to the leading end side by the pushing operation of the finger engaging member 49 arranged in the operating section 48 of the grasping forceps 40 for the endoscope. Thereupon, the elastic grasping members 41, 42, 43, 44, 45 arranged at the position of the leading end member 51 and the coil sheath 52 on the leading end side disposed on the insertion section leading end side of the grasping forceps 40 for the endoscope are pushed out from the insertion section leading end surface 46a. At that time, owing to the elastic restoring forces and the flexing habits of the respective elastic grasping members 41, 42, 43, 44, 45, the circular pawl portions 41a, 42a, 43a, 44a, 45a formed at the leading end portions of the respective elastic grasping members are arranged in the helical manner as shown in FIG. 5 and spread outwards from the center axis of the insertion section 46 so as to be arranged along the circle of a diameter at least 20 mm in the spread state.

Subsequently, the finger engaging member 49 of the operating section 48 is operationally pulled. Thereupon, the operating wire 55 is moved to the hand side, and the elastic grasping members 41, 42, 43, 44, 45 are gradually accommodated into the interiors of the leading end member 51 and the coil sheath 52 on the leading end side of the insertion section 46. At that time, the circular pawl portions 41a, 42a, 43a, 44a, 45a are gradually closed toward the center axis of the insertion section 46 according to the order of the shortest one to the longest one to grasp the living body tissue or the foreign body in the longitudinally converged and side by side arranged state.

After all, the grasping forceps 40 for the endoscope which has grasped the cellular tissue or the foreign body by the elastic grasping section 47 is pulled out of the body cavity to complete the recovering of the cellular tissue or the foreign body.

In that way, since there are provided at least four elastic grasping members constructing the elastic grasping section, it becomes possible to narrow the gaps between the adjacent elastic grasping members constructing the elastic grasping section. Thereby, it becomes possible to recover the once grasped living body tissue or foreign body without dropping it through the gaps between the adjacent elastic grasping members within the body cavity.

Figure 5:
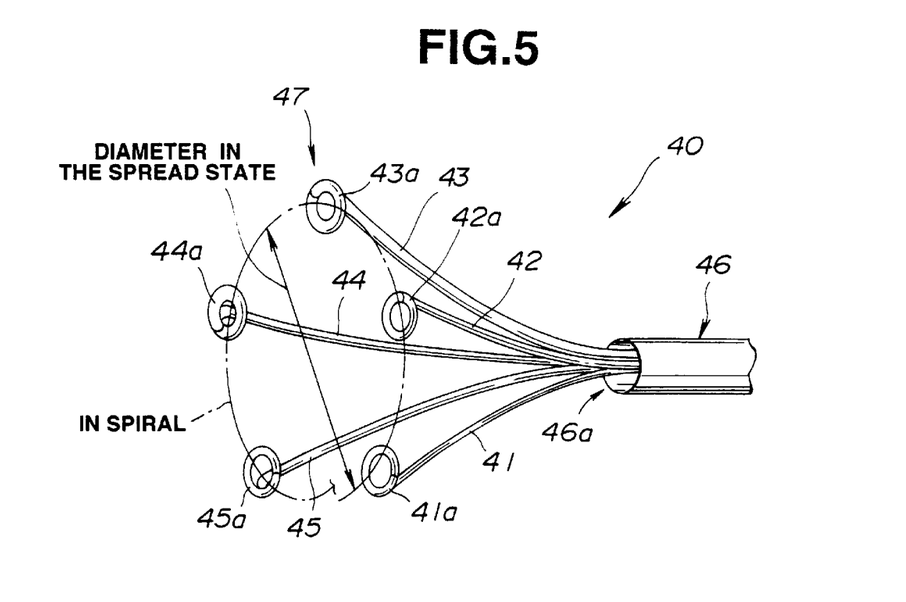

Since the lengths of the respective elastic grasping members from their hand side ends to their leading end portions are changed as well as the elastic grasping members have the habits of so flexing that the leading end grasping portions are spread in the helical manner (as shown in FIG. 5), when the elastic grasping members in the spread state are closed, the elastic grasping members and the leading end grasping portions can be closed orderly and converged without the entangling of the elastic grasping members.

Further, since there are provided at least four elastic grasping members constructing the elastic grasping section, it becomes possible to make the wire diameters of the elastic grasping members thinner than those of the conventional elastic grasping members of the elastic grasping section composed of three elastic grasping members without widening the gaps between the adjacent elastic grasping members formed of the stainless steel wire, the spring stainless steel wire or the like. Thereby, the flexing degree of each elastic grasping member becomes larger. Especially, when the spring stainless steel is used for the elastic grasping members, the spring effects are remarkably improved so as to enable not only the soft grasping of the living body tissue or the like but also the easy setting of the spread diameter of the elastic grasping section to at least 20 mm.

Since the elastic grasping members are formed by the stainless steel wire or the spring stainless steel wire, it is possible to remarkably improve the corrosion resisting characteristic of the elastic grasping section which is brought into contact with body liquids, steam generated by an autoclave and so on.

Figure 6:
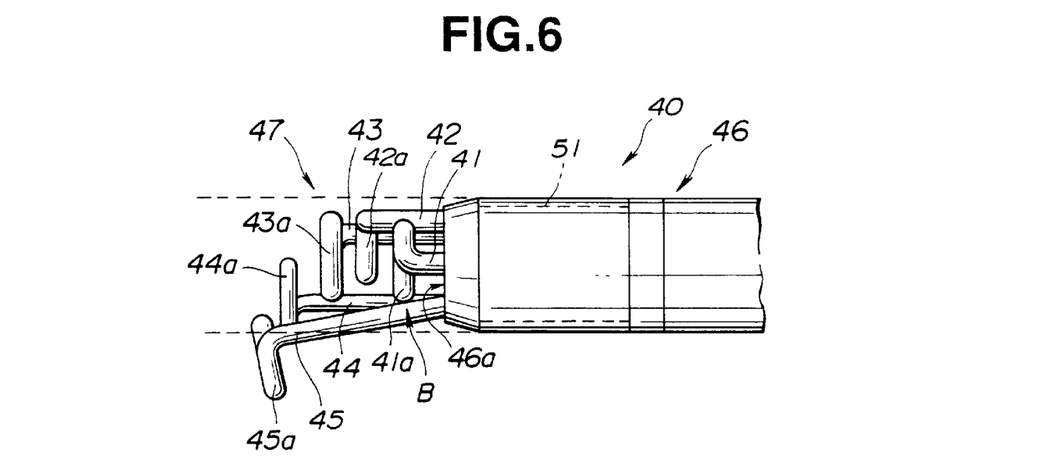
FIG. 6 is an explanatory view showing a midway state of the closing of the elastic grasping section of the grasping forceps for the endoscope composed of five elastic grasping members of different lengths.

But, as shown in FIG. 6, while the spread elastic grasping section 47 of the grasping forceps 40 for the endoscope provided with, for example the five elastic grasping members 41, 42, 43, 44, 45 described in the above-mentioned first embodiment is pulled into the internal bore of the cylindrical leading end member 51, when the leading end grasping portion 41a disposed nearest to the insertion section leading end surface 46a and the elastic grasping member 45 having the leading end grasping portion 45a disposed remotest from the insertion section leading end surface 46a are brought into contact with each other as indicated by B in FIG. 6, it is apprehended that the elastic grasping member 45 is pushed out beyond the extension line (depicted by the broken line) of the outer peripheral surface of the insertion section 46.

Figure 7:
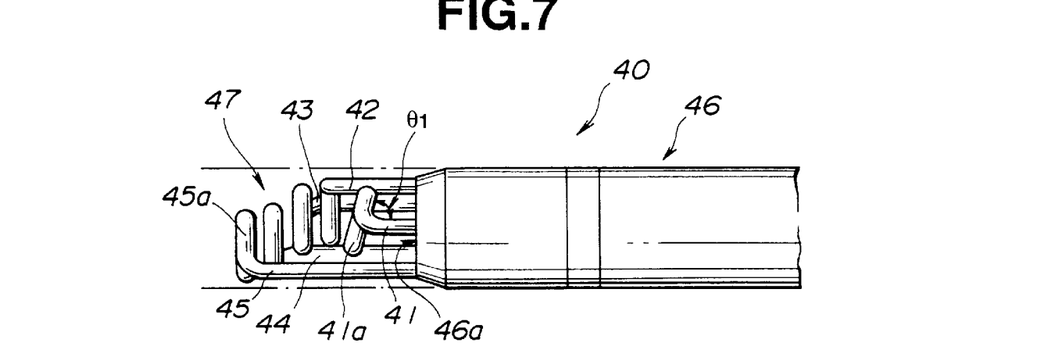
FIG. 7 is an explanatory view of a construction of an elastic grasping section of a grasping forceps for an endoscope according to the second embodiment of the present invention.

Then, a second embodiment of the present invention will be explained with reference to FIG. 7.

As illustrated, the elastic grasping section 47 of the grasping forceps 40 for the endoscope which is capable of recovering the tissue as the object within the body cavity comprises the five elastic grasping members 41, 42, 43, 44, 45 and the circular pawl portions 41a, 42a, 43a, 44a, 45a substantially circularly curved as the leading end grasping portions at the leading end portions of the elastic grasping members 41, 42, 43, 44, 45.

The circular pawl portions 41a, 42a, 43a, 44a, 45a are bent smoothly inwards relative to the advancing and retreating direction of the operating wire 55, and in order to arrange the circular pawl portion 41a disposed nearest to the insertion section leading end surface 46a and the elastic grasping member 45 having the circular pawl portion 45a disposed remotest from the insertion section leading end surface 46a in an inclined relationship, the circular pawl portion 41a and the elastic grasping member 45 are prevented from contact with each other by setting an inclination angle θ1 to an acute angle relative to the elastic grasping member 45. Other constructions are the same as those in the first embodiment and designated by the same symbols to omit the explanations about them.

The functions of the grasping forceps 40 for the endoscope having the above-mentioned constructions will be explained.

First of all, under the condition that the operating wire 55 of the grasping forceps 40 for the endoscope has been pulled, namely under the condition that the circular pawl portions 41a, 42a, 43a, 44a, 45a of the elastic grasping section 47 have been closed, the grasping forceps 40 for the endoscope is inserted into the body cavity through the treating instrument passing channel of the endoscope 10 introduced near to the polypus.

Then, the operating wire 55 is moved to the leading end side by operatingly pushing and pulling the finger engaging member 49 arranged in the operating section 48 of the grasping forceps 40 for the endoscope. Thereupon, the elastic grasping section 47 located within the leading end member 51 and the coil sheath 52 on the leading end side disposed on the insertion section leading end side of the grasping forceps 40 for the endoscope are pushed out from the insertion section 46. At that time, the circular pawl portions 41a, 42a, 43a, 44a, 45a formed at the leading end portions of the respective elastic grasping members are spread outwards with respect to the center axis of the insertion section 46 by the restoring forces and the flexing habits of the respective elastic grasping members 41, 42, 43, 44, 45.

Subsequently, the operating wire 55 is moved to the hand side by operationally pulling the finger engaging member 49 of the operating section 48. Thereupon, the elastic grasping members 41, 42, 43, 44, 45 are gradually accommodated into the interiors of the leading end member 51 and the coil sheath 52 on the leading end side of the insertion section 46 as well as the circular pawl portions 41a, 42a, 43a, 44a, 45a are gradually closed toward the center axis of the insertion section 46 to grasp the polypus. At that time, since the inclination angle θ1 is set to the acute angle for preventing the contact between the circular pawl portion 41a and the elastic grasping member 45, the leading end portion of the elastic grasping member 45 and the circular pawl portion 45a can be converged smoothly without being pushed outwards beyond the extension line (depicted by the alternate long and short dash line) of the outer peripheral surface of the insertion section 46.

Then, the grasping forceps 40 for the endoscope grasping the living body tissue or the foreign body in the closed state of the elastic grasping section 47 is pulled out of the body cavity together with the endoscope 30 to recover the cellular tissue or the foreign body.

In this way, since the leading end grasping portions disposed nearest to the insertion section leading end surface is so bent that the inclination angle θ1 thereof relative to the elastic grasping member having the leading end grasping portion disposed remotest from the insertion section leading end surface becomes the acute angle, when the elastic grasping section is accommodated into the insertion section by operationally pulling the operating wire, the leading end grasping portion or the leading end portion of the elastic grasping member is prevented from being pushed outwards beyond the outer peripheral surface of the insertion section by the contact between the elastic grasping portion disposed nearest to the insertion section leading end surface and the elastic grasping member having the leading end grasping members disposed remotest from the insertion section leading end surface. Thereby, the elastic grasping members constructing the elastic grasping section are reliably located inside of the extension line of the outer peripheral surface of the insertion section and converged smoothly in the side by side lined state along the longitudinal direction of the insertion section.

Further, since the elastic grasping portion disposed nearest to the insertion section leading end surface is bent at the inclination angle θ1 relative to the elastic grasping member having the leading end grasping portion disposed remotest from the insertion section leading end surface, it becomes unnecessary to form the diameter of the circular pawl portion to be disposed nearest to the insertion section leading end surface smaller than those of other circular pawl portions of the elastic grasping section and they can be formed in the same diameter of the other circular pawl portions of the elastic grasping section.

Figure 8:
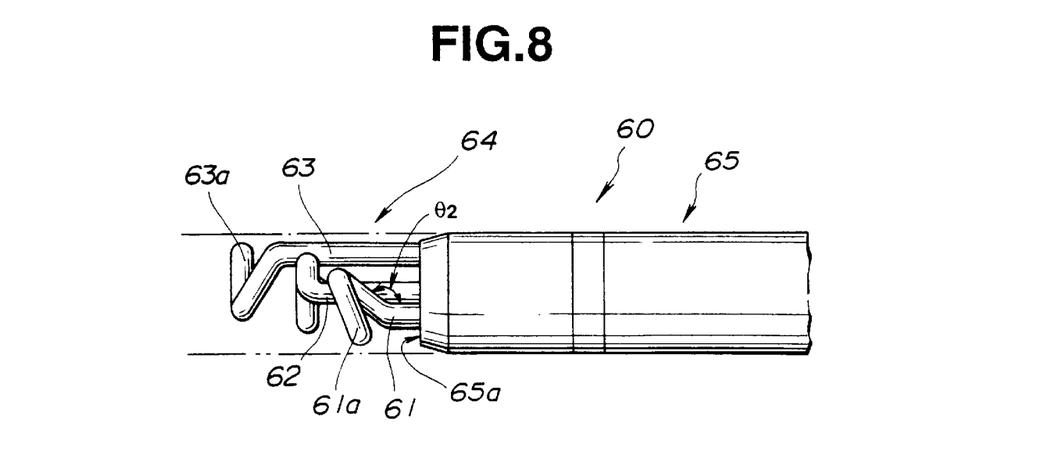
FIG. 8 is an explanatory view of another construction of the elastic grasping section of the grasping forceps for the endoscope according to the second embodiment of the present invention.

Incidentally, the construction of this embodiment is not limited to the grasping forceps 40 for the endoscope provided with the elastic grasping section 47 composed of the five elastic grasping members 41, 42, 43, 44, 45 as described above, but may be a grasping forceps 60 for the endoscope provided with an elastic grasping section 64 composed of, for example three elastic grasping members 61, 62, 63 as shown in FIG. 8.

In this case, for example as illustrated, an inclination angle θ2 of a circular pawl portion 61a disposed nearest to an insertion section leading end surface 65a of the elastic grasping members 61, 62, 63 constructing the elastic grasping section 64 relative to the elastic grasping member 63 having a circular pawl portion 63a disposed remotest from the insertion section leading end surface 65a is set to an obtuse angle. Thereby, the circular pawl portion 61a is prevented from coming in contact with the elastic grasping member 63, so that the leading end portion or the circular pawl portion 63a of the elastic grasping member 63 is not projected outwards beyond the extension line (depicted by the alternate long and short dash line) of the outer peripheral surface of the insertion section 65 to enable to obtain the same functions and effects as those of the grasping forceps 40 for the endoscope according to the second embodiment in which the inclination angle 61 is set to the acute angle.

Figure 9:
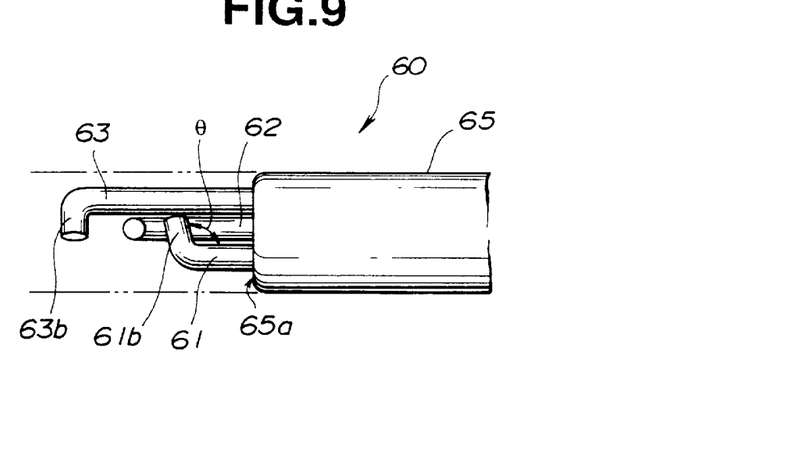
FIG. 9 is an explanatory view of another construction of the leading end grasping portions of the elastic grasping section of the grasping forceps for the endoscope.

Though the leading end grasping portions formed at the leading ends of the elastic grasping members in the above first embodiment and the second embodiment are explained as the circular pawl portions, specifications of the leading end grasping portions are not limited to the circular pawl portions but may be bent pawl portions 61b, 62b, 63b formed by bending the leading end portions of the elastic grasping members 61, 62, 63, for example inwards about 1 mm and so on as shown in FIG. 9.

Further, in the elastic grasping section 64, an inclination angle θ between the bent pawl portion 61b disposed nearest to the insertion section leading end surface 65a and the elastic grasping member 63 having the bent pawl portion 63b disposed remotest from the insertion section leading end surface 65a is set to, for example an obtuse angle. Thereby, since the bent pawl portion 61b is not brought into contact with the elastic grasping member 63, the leading end portion or the bent pawl portion 63b of the elastic grasping member 63 is not projected outwards beyond the extension line of the outer peripheral surface of the insertion section 65. Since this bent pawl portion 61a is inclined relative to the elastic grasping member 63, it becomes possible to accommodate all the bent pawl portions 61a, 62a, 63a inside of the outer peripheral surface of the insertion section in the lined up state by equalizing the length of the bent pawl portion 61a to be disposed nearest from the insertion section leading end surface 65a with the lengths of the other bent pawl portions 62a, 63a.

Though the bent pawl portions are applied to the elastic grasping section having the three elastic grasping members in above-mentioned FIG. 9, the number of the elastic grasping members of the elastic grasping section having the bent pawl portions formed therein is not limited to three but may be at least four for the elastic grasping section. Further, the inclination angle θ of the bent pawl portion is not limited to the obtuse angle but may be set to the acute angle. A chamfering is applied to edge portion formed along the periphery of the bent pawl portion so as not to injure the interior of the body cavity and the like.

As described in this above-mentioned embodiment, by applying such a construction that the leading end grasping portion disposed nearest to the insertion section leading end surface and the elastic grasping member having the leading end grasping portion disposed remotest from the insertion section leading end surface are in the inclined relationship of the inclination angle θ defined therebetween to the grasping forceps for the endoscope provided with the elastic grasping section composed of the plurality of the elastic grasping members, it becomes possible to prevent the leading end portion of the elastic grasping member or the circular pawl portion of the elastic grasping member from being pushed outwards beyond the extension line of the outer peripheral surface of the insertion section.

Figure 10A:
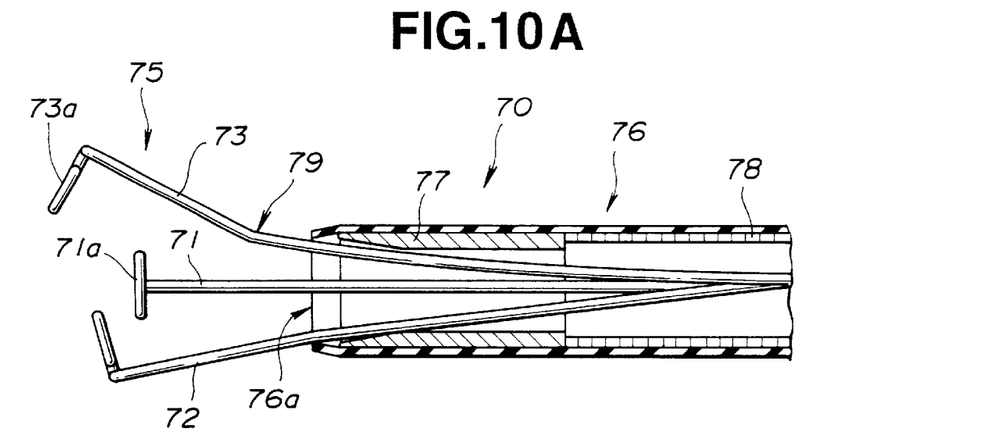
FIG. 10A is an explanatory view showing a construction and a spread state of an elastic grasping section of a grasping forceps for an endoscope.

A third embodiment of the present invention will be explained with reference to FIG. 10A and FIG. 10B.

As illustrated, since an elastic grasping section 75 of a grasping forceps 70 for an endoscope of this embodiment provided with an elastic grasping section composed of a plurality of elastic grasping members comprises, for example three elastic grasping members 71, 72, 73. In order to arrange a circular pawl portion 71a disposed nearest to an insertion section leading end surface 76a and an elastic grasping member 73 having a circular pawl portion 73a disposed remotest from the insertion section leading end surface 76a in an inclined relationship, a bent portion 79 is formed nearly at a middle portion of a leading end portion of the elastic grasping member 73 to be accommodated into the locations of a leading end member 77 and a coil sheath 78 on the leading end side constructing the insertion section 76 instead of the bending for setting the inclination angle of the circular pawl portions 41a, 61a disposed nearest to the insertion section leading end surface 46a relative to the elastic grasping members 45, 63 in the above-mentioned embodiment.

That is, the circular pawl portion 71a to be disposed nearest to the insertion section leading end surface 76a is bent inwards about at an angle of 90 degree relative to the elastic grasping member 71 as well as the bent portion 79 is formed in the elastic grasping member 73 having the circular pawl portion 73a to be disposed remotest from the insertion section leading end surface 76a so as to spread the elastic grasping member 73 outwards from the center axis. Thereby, when the elastic grasping section 75 is changed from the spread state to the closed state by operationally pulling the operating wire, the circular pawl portion 71a to be disposed nearest to the insertion section leading end surface 76a is prevented from being brought into contact with the elastic grasping member 73 having the circular pawl portion 73a to be disposed remotest from the insertion section leading end surface 76a. The other constructions are the same as those of the second embodiment and designated by the same symbols to omit the explanations about them.

The functions of the grasping forceps 70 for the endoscope having the above-mentioned construction will be explained.

When the elastic grasping section 75 of the grasping forceps 70 for the endoscope is made to spread, the operating wire is moved to the leading end side by operationally pushing the finger engaging member arranged in the operating section (not illustrated) of the grasping forceps 70 for the endoscope. Thereupon, as shown in FIG. 10A, the elastic grasping members 71, 72, 73 arranged at the locations of the leading end member 77 on the insertion section leading end side and the coil sheath 78 on the leading end side of the grasping forceps 70 for the endoscope are pushed out of the leading end surface 76a of the insertion section 76. At that time, the circular pawl portions 71a, 72a, 73a are spread outwards from the center axis of the insertion section 76 by the restoring forces of the elastic grasping members 71, 72, 73.

On one hand, when this elastic grasping section 75 is closed, the operating wire is moved to the hand side by operationally pulling the finger engaging member so that the elastic grasping members 71, 72, 73 are gradually accommodated into the interiors of the leading end member 77 and the coil sheath 78 on the leading end side of the insertion section 76. Thereupon, the elastic grasping member 73 having the bent portion 79 is brought into contact with the inner peripheral surface of the leading end member 77 so that the leading end grasping portion 73a is gradually closed. At that time, since the leading end side is spread outwards with respect to the center axis of the insertion section by the bent portion 79 formed in the elastic grasping member 73, it is accommodated without contact between the elastic grasping member 73 and the leading end grasping portion 31a to be disposed nearest to the insertion section leading end.

Figure 10B:
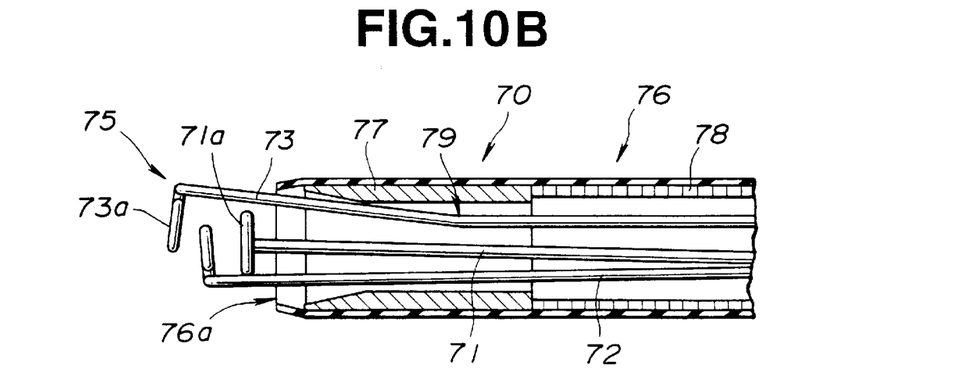
FIG. 10B is an explanatory view showing a construction and an accommodated state of the elastic grasping section of the grasping forceps for the endoscope.

When the operating wire is further pulled, as shown in FIG. 10B, the bent portion 79 of the elastic grasping member 73 passes through the inner peripheral surface of the leading end member 77 and the outwards spread elastic grasping member 73 comes into contact with the inner peripheral surface of the leading end member 77. Thereupon, the leading end grasping portion 73a or the leading end portion of the elastic grasping member 73 is converged inside of the extension line of the outer peripheral surface of the insertion section 76 and in the lined up state along the insertion section longitudinal direction without contact between the circular pawl portion 71a to be disposed nearest to the insertion section leading end surface 76a and an outwards spread portion of the elastic grasping member 73 having the leading end grasping portion 73a to be disposed remotest from the insertion section leading end surface 76a. The other functions and effects are the same as those of the above-mentioned embodiment.

Incidentally, assemblies of the grasping forceps 40, 60 for the endoscope according to the second embodiment and of the grasping forceps 70 for the endoscope according to the third embodiment will be explained.

In the grasping forceps for the endoscope according to the second embodiment, since the respective elastic grasping members have individual differences, it is difficult to previously set the inclination angle so as to prevent the contact between the elastic grasping member and the circular pawl portion. Therefore, the inclination angle is adjusted after the assembly of the grasping forceps for the endoscope so as to prevent the contact between the elastic grasping member and the circular pawl portion.

On the other hand, in the grasping forceps for the endoscope according to the third embodiment, it is difficult to previously set an angle of the bent portion for preventing the leading end portion or the circular pawl portion of the elastic grasping member from being pushed outwards beyond the outer peripheral surface of the insertion section by the contact between the elastic grasping member and the circular pawl portion for the similar reason to the above-mentioned second embodiment. But, it is possible to obtain such a merit that stress doesn't concentrate at the bent portion because a bending angle at the time of adjustment is small and the adjustment after the assembly is carried out easier than that of the grasping forceps for the endoscope according to the second embodiment.

Figure 11:
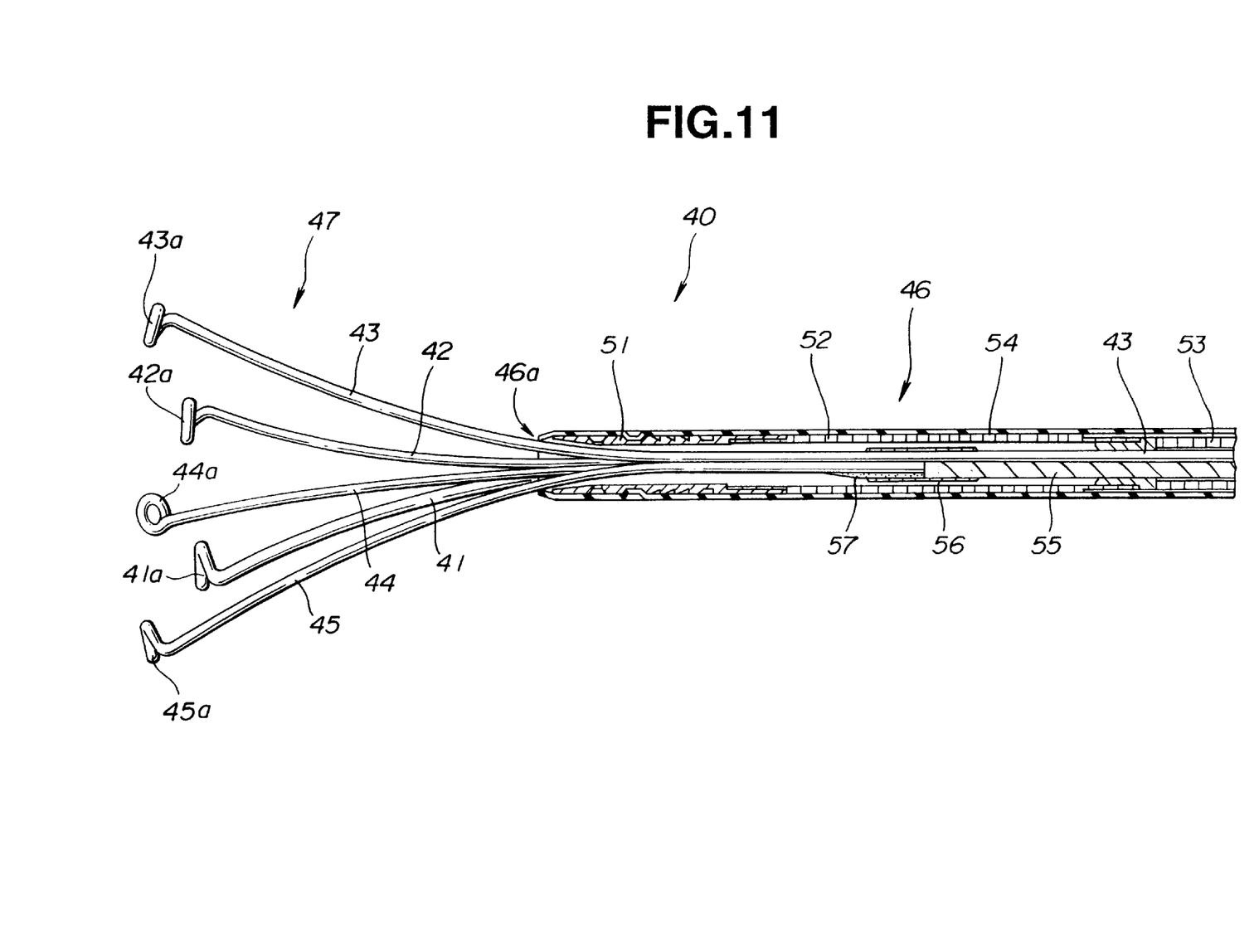
FIG. 11 is an explanatory sectional view of a leading end portion of a grasping forceps for an endoscope according to a fourth embodiment of the present invention.

A fourth embodiment of the present invention will be explained with reference to FIG. 11.

As illustrated, in this embodiment, at least one elastic grasping member, for example an elastic grasping member 43 of five elastic grasping members 41, 42, 43, 44, 45 constructing an elastic grasping section 47 is introduced to an operating section of a grasping forceps 40 for an endoscope and connected to a finger engaging member together with an operating wire 55. A midway portion of the elastic grasping member 43 to be introduced to the operating section and end portions of other elastic grasping members 41, 42, 43, 44, 45 are collectively fixedly secured into a coupling tube, and the leading end portion of the operating wire 55 is fixedly secured in the coupling tube. The other constructions are the same as those illustrated in FIG. 4A of the first embodiment, and the same component members are designated by the same symbols to omit the explanations about them.

In this way, since at least one elastic grasping member of the plurality of elastic grasping members constructing the elastic grasping section is introduced to the operating section of the grasping forceps for the endoscope in parallel to the operating wire and connected to the finger engaging member, if the operating wire is disconnected from the coupling tube by any chance, at least one elastic grasping member keeps the connection to the operating section. Therefore, it becomes possible to prevent the elastic grasping member from dropping out of the insertion section. The other functions and effects are the same as those of the above-mentioned embodiments.

A fifth embodiment of the present invention will be explained with reference to FIG. 12.

When the number of the elastic grasping members constructing the elastic grasping section is set to at least four, even through an inner diameter of the leading end member of the insertion section for accommodating the elastic grasping members is set as large as possible as well as wire diameters of the respective elastic grasping members are set as thin as possible, it becomes difficult to provide for a space for disposing a grasping section dropout prevention pin 17 at the leading end member 16 of the insertion section 15 as illustrated in FIG. 1B.

Figure 12A:
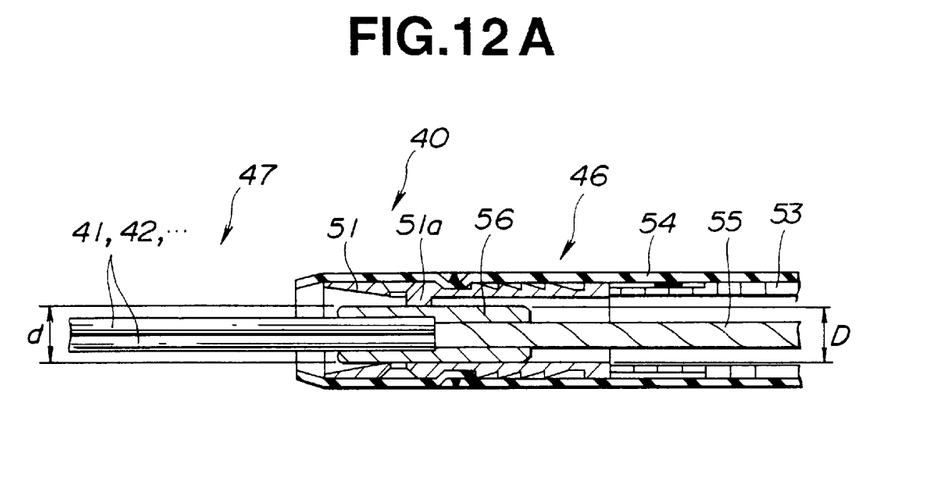
FIG. 12A is an explanatory sectional view of a leading end portion of a grasping forceps for an endoscope with a leading end member provided with a dropout preventing means.

Therefore, in this embodiment, as shown in FIG. 12A, in order to prevent the dropout of the coupling tube 52 for fixing the plurality of elastic grasping members 41, 42, ..., a convex portion 51a is formed as an elastic grasping section dropout prevention means in the inner peripheral surface of the leading end member 51 of the grasping forceps 40 for the endoscope. An inner diameter d of a through-hole defined by the leading end surface of the convex portion 51a formed in the inner peripheral surface of the leading end member 51 and the leading end member inner peripheral surface is made larger than an outer diameter D of the coupling tube 56 and set to substantially an equal dimension as far as the relationship of d>D is established. This is a reason why the coupling tube 56 for fixing the elastic grasping members 41, 42, . . . and the operating wire 55 is enabled to pass through the interior of the insertion section from the insertion section leading end surface side at the time of assembly of the grasping forceps 40 for the endoscope.

Incidentally, since the convex portion 51a of the leading end member inner peripheral surface is provided on one end side by machining or pin arrangement, a center axis of the insertion section 46 and a center axis of the through-hole defined by the leading end surface of the convex portion 51a provided in the leading end member 51 and the leading end member inner peripheral surface doesn't become coaxial. The other constructions are the same as those of the above-mentioned fourth embodiment and the same component members are designated by the same symbols to omit the explanations about them.

Functions of the grasping forceps 40 for the endoscope having the above-mentioned construction will be explained.

The operating wire 55 is moved to the leading end side by operationally pushing the finger engaging member arranged in the operating section of the grasping forceps 40 for the endoscope. Thereupon, the coupling tube 56 located within the leading end member 51b and the coil sheath 52 on the leading end side arranged on the insertion section leading end side of the grasping forceps 40 for the endoscope is moved to the convex portion side to push the elastic grasping members 41, 42 . . . out of the leading end surface 46a of the insertion section 46. The circular pawl portions (not illustrated) formed at the leading end portions of the elastic grasping members 41, 42 . . . are spread outwards from the center axis of the insertion section 46 by the elastic restoring forces of the respective elastic grasping members.

Figure 12B:
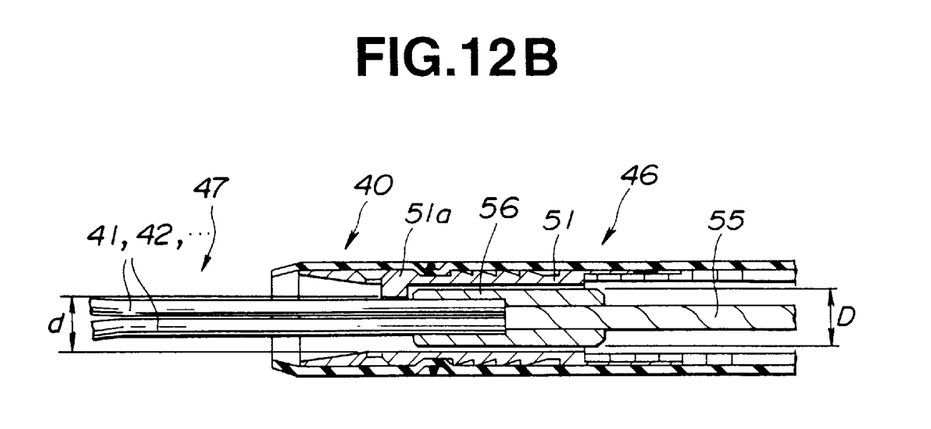
FIG. 12B is an explanatory sectional view of a function of the grasping forceps for the endoscope with the dropout preventing means.

At that time, as shown in FIG. 12B, the outer diameter D of the coupling tube 56 and the inner diameter d of the through-hole at a location where the convex portion 51a of the leading end member 51 is arranged are substantially equal to each other. When the coupling tube 56 connected to the operating wire 55 is moved through the insertion section during the operation, the center axis of the coupling tube 56 seldom coincides coaxially with the center axis of the through-hole. Therefore, the leading end surface of the coupling tube 56 catches the convex portion 51a of the leading end member 51, so that the coupling tube 56 is prevented from passing through the through-hole portion of the leading end member 51 and dropping outwards from the insertion section 46.

If the fixing portion between the operating wire 55 and the coupling tube 56 is broken by any chance, the coupling tube 56 comes in contact with the convex portion 51a so that the dropout of the elastic grasping section 47 into the body cavity can be prevented.

In this way, since the convex portion is formed on one side of the inner peripheral surface of the leading end member constructing the insertion section of the grasping forceps for the endoscope, the inner diameter of the through-hole defined by the leading end surface of the convex portion formed in the inner peripheral surface of the leading end member and the leading end member inner peripheral surface is made larger than the outer diameter of the coupling tube and set to substantially the equal dimension as far as the relationship of the inner diameter>the outer diameter of the coupling tube is established, and the center axis of the through-hole defined by the leading end surface of the convex portion formed in the inner peripheral surface of the leading end member and the leading end member inner peripheral surface is eccentric to the center axis of the insertion section, it is possible to prevent the dropout of the elastic grasping section from the insertion section. The other functions and effects are the same as those of the above-mentioned embodiments. Incidentally, the elastic grasping section drop out prevention means according to this embodiment may be disposed in the leading end member regardless of the number of the elastic grasping members constructing the elastic grasping section.

It will be apparent that various different modifications can be made widely without departing from the spirit and scope of the invention. Accordingly, it is not intended that the invention is limited, except as by the appended claims.

What is claimed is:

1. A grasping forceps for an endoscope comprising:
   a flexible insertion section;
   an operating wire passing through said insertion section and adapted to be advanced and retreated in accordance with an operation of an operating section connected to a hand side end of the operating wire; and
   an elastic grasping section arranged in the leading end portion of said operating wire and composed of at least four elastic grasping members different in length having a habit of flexing such that leading end grasping portions formed at the leading ends of said elastic grasping members spread outward from a center axis of said insertion section;
   wherein said leading end grasping portions formed at the leading ends of said at least four elastic grasping members different in length are spread in a helical arrangement at the time of spreading of said elastic grasping section so that said leading end grasping portions are arranged in a helical manner on an outer surface of an imaginary column parallel to a direction of the axis of the insertion section.

2. A grasping forceps for an endoscope comprising:
   a flexible insertion section;
   an operating wire passing through said insertion section and adapted to be advanced and retreated in accordance with an operation of an operating section connected to a hand side end of the operating wire; and
   an elastic grasping section arranged in the leading end portion of said operating wire and composed of a plurality of elastic grasping members different in length having a habit of flexing such that leading end grasping portions formed at the leading ends of said elastic grasping members spread outwards from a center axis of said insertion section;
   wherein at least a nearest leading end grasping portion disposed nearest to the insertion section and a farthest leading end grasping portion disposed farthest from the insertion section are respectively attached to first and second elastic grasping members at different angles such that said nearest leading end grasping portion and said furthest leading end grasping portion are inclined at different angles at the time of accommodating of said elastic grasping section.

3. A grasping forceps for an endoscope as set forth in claim 1 or claim 2, wherein a stainless steel wire or a spring stainless steel wire is used for said elastic grasping member.

4. A grasping forceps for an endoscope as set forth in claim 1 or claim 2, wherein a diameter of said elastic grasping section in the spread state is at least 20 mm.

5. A grasping forceps for an endoscope as set forth in claim 2, wherein said farthest leading end grasping portion disposed farthest to said insertion section is bent at an inclination angle substantially different from ninety degrees with respect to the elastic grasping member to which said farthest leading end grasping portion is attached, so that said nearest leading end grasping portion disposed nearest to said insertion section, and said farthest leading end grasping portion disposed farthest from said insertion section are inclined at different angles.

6. A grasping forceps for an endoscope as set forth in claim 5, wherein the inclination angle between said nearest leading end grasping portion, disposed nearest to said insertion section, and said first elastic grasping member is an obtuse angle.

7. A grasping forceps for an endoscope as set forth in claim 5, wherein the inclination angle between said nearest leading end grasping portion, disposed nearest to said insertion section, and said first elastic grasping member is an acute angle.

8. A grasping forceps for an endoscope as set forth in claim 2, wherein a bent portion is formed in said second elastic grasping member having said farthest leading end grasping portion disposed farthest from said insertion section, so that said nearest leading end grasping portion disposed nearest to said insertion section and said elastic grasping member having said farthest leading end grasping portion disposed farthest from said insertion section are inclined at different angles when said elastic grasping members are spread.

9. A grasping forceps for an endoscope as set forth in claim 8, wherein leading end side portions of said elastic grasping members are spread outwards from the center axis of the insertion section by the bent portion formed nearly in a midway portion of said second elastic grasping member having said farthest leading end portion attached.

10. A grasping forceps for an endoscope as set forth in claim 1 or claim 2, wherein at least one of said elastic grasping members different in length is extended to said operating section.

11. A grasping forceps for an endoscope as set forth in claim 1 or claim 2, wherein said leading end grasping portions are circular pawl portions.

12. A grasping forceps for an endoscope as set forth in claim 1 or claim 2, wherein said leading end grasping portions are bent pawl portions.

13. A grasping forceps for an endoscope including an insertion section comprising:

at least a leading end member and a flexible sheath, an operating wire adapted to pass through said insertion section, a plurality of elastic grasping members having a habit of flexing so that leading end grasping portions arranged at a leading end portion of said operating wire and formed at the leading ends of said elastic grasping members spread outward from a center axis of said insertion section, and elastic grasping section drop-out prevention means arranged in an inner peripheral surface of said end member for preventing said plurality of elastic grasping members from dropping out, wherein a cross section of the combination of the elastic grasping section drop-out prevention means and the leading end member, taken in a direction perpendicular to a center axis of the inner peripheral surface of the leading end member, includes a through-hole having a center spaced apart from the center axis of the inner peripheral surface of the leading end member.

14. A grasping forceps for an endoscope as set forth in claim 13, wherein the through-hole is part of a tubular hole portion defined in said elastic grasping section drop-out prevention means, and wherein a center axis of the tubular hole portion and a center axis of the inner peripheral surface of the leading end member are spaced apart.

15. The grasping forceps according to claim 14, wherein the tubular hole defined in said elastic grasping section drop-out prevention means is cylindrically shaped.

16. A grasping forceps for an endoscope as set forth in claim 13, wherein the inner peripheral surface of said leading end member and an inner peripheral surface of said drop-out prevention means include portions which are cylindrically shaped having substantially parallel and spaced apart axes, and wherein the diameter of the cylindrically shaped portion of the inner peripheral surface of said drop-out prevention means is equal to or larger than the diameter of a coupling member coupling the plurality of grasping members.

17. The grasping forceps according to claim 13, wherein the center of the through-hole is defined such that any line including the center of the through-hole lying in the plane of the cross section equally divides the area of the through-hole.

18. The grasping forceps according to claim 13, wherein a shape of the through-hole is symmetrical with respect to the center of the through-hole.

19. The grasping forceps according to claim 13, wherein the through-hole is circular.

20. The grasping forceps according to claim 13, wherein the through-hole is completely defined by said drop-out prevention means.

* * * * *